United States Patent [19]

Dopper et al.

[11] Patent Number: 5,527,543
[45] Date of Patent: Jun. 18, 1996

[54] PHARMACEUTICAL GRANULATE

[75] Inventors: Jan H. Dopper, Oss; Cornelis J. M. Van Der Ven, Uden, both of Netherlands

[73] Assignee: Akzo Nobel N.V., Arnhem, Netherlands

[21] Appl. No.: 366,348

[22] Filed: Dec. 29, 1994

Related U.S. Application Data

[62] Division of Ser. No. 941,026, Sep. 4, 1992, Pat. No. 5,395,627.

[51] Int. Cl.$^6$ ...................................................... A61K 9/14
[52] U.S. Cl. ........................... 424/489; 424/458; 424/465
[58] Field of Search .................................. 424/489, 490, 424/465, 488, 78.31

[56] References Cited

U.S. PATENT DOCUMENTS

| | | | |
|---|---|---|---|
| 4,180,560 | 12/1979 | Katz et al. | 424/21 |
| 4,729,895 | 3/1988 | Makino et al. | 424/465 |
| 4,871,548 | 10/1989 | Edgren et al. | 424/488 |
| 4,914,089 | 4/1990 | Tax et al. | 544/170 |
| 5,035,897 | 6/1991 | Ayer et al. | 424/473 |
| 5,145,675 | 9/1992 | Won | 424/78.31 |
| 5,200,194 | 4/1993 | Edgren et al. | 424/473 |
| 5,284,662 | 2/1994 | Koparkar et al. | 424/473 |

FOREIGN PATENT DOCUMENTS

| | | |
|---|---|---|
| 0375063 | 6/1990 | European Pat. Off. |
| A-0491443 | 6/1992 | European Pat. Off. |
| A-93/13760 | 7/1993 | WIPO |

*Primary Examiner*—Thurman K. Page
*Assistant Examiner*—William E. Benston, Jr.
*Attorney, Agent, or Firm*—Mary E. Gormley

[57] ABSTRACT

Disclosed is a process of preparing granules involving first preparing a carrier comprising diluent, binder, and optionally a disintegrating agent. In a container separate from said carrier, a steroid, lubricant and, optionally, an antioxidant are dissolved in an, optionally pre-heated, organic solvent. The resulting solution is added to the carrier contained within an, e.g. vacuum mixer, followed by further blending of the mixture. The organic solvent is removed from the mixture. The mixture is blended further to form granules. The process may further include incorporating a flow enhancer such as colloidal silicon dioxide into the granules. A granule for making a pharmaceutical dosage unit is granule characterized in comprising: a) a carrier comprising diluent and binder, and b) a film coating said carrier, said film comprising desogestrel and a lubricant, and has the characteristic of by retaining 90% of the desogestrel at a pressure of 150 mbar and at a temperature of 70° C. over 72 hours.

12 Claims, No Drawings

PHARMACEUTICAL GRANULATE

This is a division of application Ser. No. 07/941,026 filed Sep. 4, 1992, now U.S. Pat. No. 5,956,627.

TECHNICAL FIELD

This invention relates to pharmaceutical compositions generally, and more specifically to pharmaceutical granulates and processes for making them.

BACKGROUND ART

Methods for making tablets and other solid or dry pharmaceutical preparations are well-known. For example in the standard text Chase, et al., *Remington's Pharmaceutical Sciences,* pp. 1553–1576 (16th ed. 1980, Mack Publ. Co. of Easton, Pa., U.S.A.) ("Remington's"), methods of making tablets, capsules and pills and their respective components are described. Three methods of making tablets include the "wet-granulation", "dry-granulation", and direct compression methods.

Wet-granulation methods involve weighing out ingredients (including a solvent), mixing them, granulating them, screening them damp, drying them, dry screening, lubricating, and compressing the resultant admixture into tablets. See, e.g. Belgian Patent No. 773,064. Such procedures generally result in tablets having adequate tablet homogeneity.

While granules made according to these methods are adequate for many medicinal agents, they are not altogether adequate for use with certain medicinal agents and applications (e.g. for making tablets containing low doses of very potent steroids).

DISCLOSURE OF THE INVENTION

It has been found that certain steroids such as desogestrel transfer from tablets into the surrounding local environment. If the transfer of the steroid from the tablet cannot be prevented, the quantity of steroid contained within the dosage unit may drop below stated levels within a relatively short period of time.

The invention includes a process of preparing granules which, among other things, display the ability to retain compounds such as desogestrel even under extreme conditions. The process involves first mixing a carrier comprising diluent, binder, and optionally a disintegrating agent. The carrier may be prepared in a mixer or alternatively in another container, and then added to the mixer. In a container separate from the container containing the carrier, asteroid or steroids, lubricant and, optionally, an antioxidant are dissolved in a suitable organic solvent. The resulting solution is added to the carrier which, if it is not already present, is transferred to the mixer. The carrier and solution are blended. The organic solvent is then removed (e.g. by evaporation), and the mixture further blended to form steroid loaded granules (i.e. granules containing steroid).

After removal of the organic solvent, the steroid loaded granules may be mixed with a flow enhancer such as colloidal silicon dioxide.

The resulting granules are remarkably homogenous, with the steroid or steroids being distributed evenly over the granules. Tablets made with the granules are very resistant to segregation. The procedure further results in a non-agglomerated drug. Micronized materials need not be used resulting in a simpler, more economic granulation process. Tablets made with the granules have excellent dissolution rates. The entire process is relatively easily scaled-up.

BEST MODE OF THE INVENTION

Various steroids can be used with the invention. Preferably the steroids used in the compositions and processes of the invention are estrogens, progestogens, or both of them.

Preferred progestogens for use with the invention include 3-ketodesogestrel ("etonogestrel"), desogestrel, levo-norgestrel, norgestrel, norethindrone, gestodene, and other compounds with progestogenic activity. Especially preferred are 3-ketodesogestrel and desogestrel.

Examples of preferred estrogens include ethinyl estradiol, mestranol and 17-α-ethinyl estradiol 3-methylether, ethyl estranol, and other compounds with estrogenic activity.

Granules according to the invention are preferably made of a) a carrier which comprises a diluent and a binder, and b) a film coating the carrier. The film coating is made of at least desogestrel and a lubricant distributed over the carrier. The granules, and pharmaceutical dosage units made with them, prevent transfer of the compound out of the dosage unit. As used herein, "transfer" includes any process in which the compound prematurely leaves the dosage unit.

Desogestrel containing granules made according to the invention have the characteristic of retaining more than 90%, preferably more than 95%, and even more preferably more than 97% of the desogestrel when stored at a pressure of 150 mbar, at a temperature of 70° C. over 72 hours.

The granules are preferably used to make a stable solid pharmaceutical unit such as a tablet, capsule, pill, dragee, or powder. A coated biconvex tablet is the presently most preferred dosage unit. Tablets made with desogestel containing granules have the characteristic of retaining more than 90%, preferably more than 95%, and even more preferably more than 98% of the desogestrel when stored at a pressure of 150 mbar, at a temperature of 70° C. over 72 hours.

The term "dosage unit" or "pharmaceutical dosage unit" generally refers to physically discrete units suitable as unitary dosages for humans or animals, each containing a predetermined quantity of active material (e.g. estrogen or progestogen) calculated to produce the desired effect. Examples of such dosage units are tablets, capsules, powders, and pills.

Methods and compositions for making various dosage units using the granules are known to those skilled in the art. For example, methods and compositions for making tablets, capsules and pills using the granules are described in Remington's at pages 1553 through 1584. Methods of coating pharmaceutical dosage units are described at pages 1585 to 1593 of the reference.

The concentration of steroid or steroids included in the granules—and eventually the dosage unit—will of course depend on the particular steroid's potency, its intended use, and the eventual mass of the dosage unit. The amount of asteroid or steroids used in a dosage unit will be well-known to those skilled in the art.

A carrier according to the invention is typically a basic granulate containing a diluent and binder. Preferably the carrier will also include a disintegrating agent.

Diluents or "filler excipients" are agents added to dosage units to increase the granules' and resulting dosage units' bulk. The preferred diluent for use in this regard is lactose. Other diluents include mannitol, sorbitol, cellulose, xylitol, dextrose, fructose, calcium phosphate, NaCaPO$_4$, sucrose, and mixtures thereof. The diluent will typically make up from 70 to 95% by weight of the resulting steroid loaded granules.

Binders are agents used to impart cohesive properties to the granules, resulting in more physically stable dosage units, and include hydroxypropylcellulose, amylopectin, starch, hydroxypropylmethylcellulose, gelatin, and starch based binders. The preferred binder for use with the invention is povidone (polyvinylpyrolidone). The binder will typically make up from 0.5 to 5% by weight of the resulting steroid loaded granules.

Disintegrating agent or "disintegrators" are substances or mixtures of substances added to a tablet to facilitate its breakup or disintegration after administration. Typically such agents are modified or unmodified starches, clays, cross-linked PVP, modified or unmodified celluloses, gums or algins. The presently most preferred agents are corn starch, potato starch, and wheat starch. Disintegrators will typically make up from 5 to 50%, preferably 5 to 15%, by weight of the resulting granules.

The carrier may be prepared in the mixer. This avoids unnecessary process steps, such as transferring the carrier to the mixer, thus also preventing possible waste. However, the carrier is preferably made in a fluidized bed granulator, and then later added to the mixer for later loading with steroid.

Mixers for use with the invention are readily commercially available and are capable of mixing or blending the dry ingredients with the organic solvent containing the steroid or steroids. Vacuum mixers which are closed to the outside environment are preferred for workers' safety and environmental reasons since the solvent is not released into the atmosphere, and can be collected for re-use. Vacuum mixers are like general mixers except they also typically have a heating jacket and vacuum connections. The production of a vacuum in the mixing environment allows for shorter drying times, lower drying temperatures, and for the exclusion of oxygen from the mixing process which may be useful for drugs which are sensitive to oxygen or heat.

The "wet" portion added to the carrier will preferably consist of the steroid or steroids, an antioxidant, and a lubricant all dissolved in an organic solvent.

Lubricants are agents which improve the rate of flow of the tablet granulation, prevent adhesion of the tablet material to the surface of dies and punches, reduce interparticle friction, and facilitate the ejection of the tablets from the die cavity. Commonly used lubricants are talc, long chain fatty acids, magnesium stearate, stearic acid, calcium stearate, polyethylene glycol, palmitic acid, and hydrogenated vegetable oils. The presently most preferred lubricant for use with the invention is stearic acid. The lubricant will typically make up from 0.25 to 3% by weight of the resulting granules.

Organic solvents for use with the invention are preferably those having a sufficiently low boiling point at the pressures attainable in the vacuum mixture to evaporate off during the process. These include acetone, methylene chloride, ethanol, methanol, isopropanol, and mixtures thereof. The binder need not be very soluble in the organic solvent. As used herein the term "organic solvent" also includes mixtures of any of the aforementioned solvents with water (e.g. acetone 80 vol. % and water 20 vol. %).

A sufficient amount of organic solvent will be used to dissolve the steroid or steroids, lubricant and antioxidant, and sufficiently wet the carrier without impairing the flow properties. Thus the amount of organic solvent used in the process will depend upon the potency and solubility characteristics of the particular steroid or steroids in the particular organic solvent, the solubility of the other components in the solvent, and the size of the batch of carrier to be wetted. Organic solvent will typically make up from 5 to 20% by weight of the mixture of solution and carrier.

The organic solvent is preferably pre-heated to a temperature less than its boiling point. Such pre-heating increases the speed of dissolution of the lubricants, antioxidants, and steroid or steroids in the solvent; results in better distribution of the components over the carrier; and eases removal of the solvent from the granules. Heating of the solvent containing steroid and lubricant is also preferably maintained during its transfer to the mixer.

The carrier may also be pre-heated before addition of the wet portion to decrease the amount of time needed to evaporate the solvent.

After removal of the solvent, a flow enhancer is preferably mixed with the drug loaded granules. The flow enhancer (e.g. colloidal silicon dioxide) acts to prevent the granules from clumping. Flow enhancers will typically make up from 0.1 to 3% by weight of the resulting mixture.

The use of other conventional additives or "further excipients", e.g. colorants, stabilizers or antioxidants, is contemplated. Stabilizers such as EDTA, polyethylene glycol (PEG), and butylated hydroxy toluene (BHT), may also be included if desired, although it is not required. The presently most preferred antioxidant for use with the invention is DL-α-tocopherol. Other medicinal agents (e.g. 17β-estradiol) may also be included in the formulation.

The granules may then be tabletted or encapsulated by means well-known to those skilled in the art. Tablets made with granules of the invention allow for much less transfer of desogestrel from the tablets than do tablets containing desogestrel made according to prior art techniques.

The invention is further explained by reference to the following illustrative examples:

EXAMPLE I

| | |
|---|---|
| Desogestrel | 150 μg |
| EE | 30 μg |
| PVP | 2.4 mg |
| Stearic acid | 0.8 mg |
| Corn starch | 6.5 mg |
| Colloidal SiO$_2$ | 0.8 mg |
| DL-α-tocopherol | 0.08 mg |
| Lactose 100M | 67.74 mg | were made by the following process.

Tablets were made by first preparing the carrier. In a vacuum mixer, 4880 g of carrier components (87% lactose, 10% corn starch, and 3% PCP) were added. The components were mixed and heated to 35° C. In a separate container, desogestrel (11.54 g), ethinyl estradiol (2.31 g), stearic acid (50.0 g), DL-α-tocopherol (6.17 g) were dissolved in 350 ml acetone, preheated to 45° C. This solution was then mixed with the carrier in a vacuum mixer (kept at 100 mbar). The beaker containing the acetone solution was then rinsed with acetone, and the wash solution transferred to the mixer. The mixture was blended for 10 min., the mass heated to a temperature of 45° C., corresponding to a jacket temperature of 47° C. Blending was stopped, and the mass allowed to cool to 15° C. The vacuum was gradually adjusted to less than mbar and the mass heated to a temperature of 45° C., while blending cnotinuously in order to evaporate the acetone. The mixture was further blended without heating until the mass reached a temperature of 20° C. forming drug loaded granules.

50 g of colloidal SiO₂ was then transferred to the mixer.

| Blending (min.) | Position | Rotation Speed (rpm) | Direction |
|---|---|---|---|
| 1 | 90° | ca. 14 | left |
| 0.5 | ca. 120° | ca. 14 | left |
| 1 | 90° | ca. 14 | right |
| 0.5 | ca. 45° | ca. 14 | right |

The resulting mixture was compressed on a rotary press to biconvex tablets. The tablet weight was adjusted to 65 mg.

EXAMPLE II

The granules and tablets of EXAMPLE I were compared with the following tablets each containing:

| | |
|---|---|
| Desogestrel (micronized) | 150 μg |
| EE (micronized) | 30 μg |
| Na starch glycolate | 1.2 mg |
| Colloidal SiO₂ | 0.9 mg |
| Mg Stearate | 0.3 mg |
| Spray-dried lactose (Pharmatose DCL-11) qsad | 60.0 mg |

These tablets were made by first dry mixing desogestrel and EE with proportionate quantities of spray dried lactose for approx. 3 min. The other ingredients were then also mixed into the mixture until for approx. 5 min. The mixture was then tabletted by direct compression.

The tablets were subjected to various conditions wherein the transfer of drug from the granule or tablet could be measured, with the following results:

A. Transfer from dosage unit

| Subject | percentage remaining (weight) |
|---|---|
| EXAMPLE I | |
| Granules | 97 |
| Tablets | 98 |
| EXAMPLE II | |
| Granules | 67 |
| Tablets | 87 |

Conditions: stored for 72 hours at a pressure of 150 mbar, at a temperature of 70° C.

B. Transfer to Packaging material

These tablets of this EXAMPLE II and the tablets of EXAMPLE I were coated with:

| | |
|---|---|
| Hydroxypropylmethylcellullose E 15 | 0.75 mg |
| PEG 400 | 0.15 mg |
| Talc | 0.19 mg |
| Titanium dioxide | 0.11 mg |
| Demineralized H₂O | to 15 μl |

Both sets of tablets were packaged in PVC/aluminum foil packs, and subjected to a test to examine the extent of transfer of desogestrel from the coated tablets to the packaging material.

Tablets made according to EXAMPLE I, and coated, lost less than 0.5% of their total steroid content to the surrounding PVC material after even 19 mos. of storage at 32° C. and 70% relative humidity. In contrast, coated tablets made as per this EXAMPLE II displayed 12.4% transfer to the packaging material after only 6 mos. at 37° C. and ambient relative humidity, and 16.2% after 6 mos. at 37° C. and at 95% relative humidity. Surprisingly, even coating of the dosage unit does not prevent migration of desogestrel.

EXAMPLE III

Content Uniformity

The content uniformity of desogestrel and EE in tablets prepared according to EXAMPLE I was determined and revealed relative standard deviations of approximately 1% (0.5 to 1.5%) indicating excellent homogeneity of the steroids throughout the tablets.

EXAMPLE IV

Segregation Stability

A sample of granulate made according to EXAMPLE I was sieved using the following sieves: –0, 75, 90, 150, 300, and 500 μm. From the different particle ranges the content of the active ingredients was determined, as was the weight fraction. The demixing potential (DP %) was calculated for the sample using the following formula:

$$DP\% = \frac{100}{\bar{p}} \left[ \sum_{i=1}^{n} \frac{w_i}{100} (p_i - \bar{p})^2 \right]^{1/2}$$

wherein $p_i$ is the proportion of drug associated with $w_i$ weight % of the mixture in sieve fraction i. The mean content was determined by:

$$\bar{p} = \frac{\sum_{i=1}^{n} p_i * w_i}{\sum_{i=1}^{n} w_i}$$

The calculated demixing potential for ethinylestradiol and desogestrel were 8.17% EE and 8.42% desogestrel, both well under the safety limit of 10%, and indicating a high stability against segregation explaining the high content uniformity shown in EXAMPLE III.

EXAMPLE V

Capsules are made by incorporating the "Excipients" portion of EXAMPLE I into capsules.

References herein to specific Examples or embodiments should not be interpreted as limitations to the extent of protection which shall be determined by the terms of the claims.

What is claimed is:

1. A process for preparing granules containing one or more steroids, comprising:
   a) dissolving one or more steroids in a lubricant in a sufficient amount of an organic solvent to form a solution;
   b) mixing the solution with a carrier comprising diluent and binder thus forming a mixture of solution and carrier; and
   c) removing the organic solvent from the mixture while blending the mixture to form said granules.

2. The process according to claim 1 wherein said organic solvent is removed in a vacuum mixer.

3. The process according to claim 1 wherein said carrier further comprises a disintegrating agent.

4. A process according to claim 1, wherein an antioxidant is included in the solution formed in step a).

5. The process according to claim 1 further comprising mixing a flow enhancer with said granules by blending the flow enhancer with the composition contained within the mixer after removal of the organic solvent.

6. The process according to claim 1 wherein the organic solvent is heated to above ambient temperature before dissolution of the steroid and lubricant therein.

7. The process according to claim 1 wherein said steroid is selected from the group consisting of desogestrel, 3-ketodesogestrel, ethinyl estradiol, norgestrel, norethindrone, 17β-estradiol, and mixtures of one or more of said group of steroids.

8. The process according to claim 1 wherein the diluent is lactose or mannitol.

9. The process of claim 3 wherein the disintegrating agent is selected from the group of starches consisting of corn starch, potato starch, wheat starch, and mixtures thereof.

10. The process according to claim 1 wherein the binder is polyvinylpyrolidone or hydroxypropylcellulose.

11. The process according to claim 1 wherein the organic solvent is selected from the group consisting of acetone, methylene chloride, ethanol, methanol, isopropanol, mixtures thereof, and mixtures thereof with water.

12. The process according to claim 1 wherein said lubricant is stearic acid.

* * * * *